(12) United States Patent
Lin (10) Patent No.: US 8,601,678 B1
(45) Date of Patent: Dec. 10, 2013

(54) MANUFACTURING METHOD OF NERVE-STIMULATING AND SIGNAL-MONITORING DEVICE

(71) Applicant: Chung Hua University, Hsinchu (TW)

(72) Inventor: Jium Ming Lin, Hsinchu (TW)

(73) Assignee: Chung Hua University, Hsinchu (TW)

( * ) Notice: Subject to any disclaimer, the term of this patent is extended or adjusted under 35 U.S.C. 154(b) by 0 days.

(21) Appl. No.: 13/964,845

(22) Filed: Aug. 12, 2013

Related U.S. Application Data (62) Division of application No. 12/767,592, filed on Apr. 26, 2010.

(30) Foreign Application Priority Data

Jul. 10, 2009 (TW) .............................. 98123308 A (51) Int. Cl.
*B23P 19/00* (2006.01)

(52) U.S. Cl.
USPC .......................................................... 29/746

(58) Field of Classification Search
USPC ...................................... 29/746, 745; 607/60
See application file for complete search history.

(56) References Cited

U.S. PATENT DOCUMENTS

2007/0233204 A1   10/2007   Lima et al.

FOREIGN PATENT DOCUMENTS

| TW | 560065 | 11/2003 |
|---|---|---|
| TW | 200846670 | 12/2008 |

OTHER PUBLICATIONS

Office Action to TW counterpart patent application No. 098123308 dated Aug. 23, 2013 citing: US 2007/0233204A1, TW 560065, TW 200846670, and Lin et al.
Lin et al. Integrating Micro Array Bio-Sensing Probes with Semiconductor Amplifier on a Flexible Substrate. 3rd International Conference on Sensing Technology. 2008.
English Translation Summary of Office Action to TW counterpart patent application No. 098123308 dated Aug. 23, 2013 citing: US 2007/0233204A1, TW 560065, TW 200846670, and Lin et al.
English Translation of Abstracts of TW 560065 and TW 200846670.

*Primary Examiner* — Christopher D Koharski
*Assistant Examiner* — Philip Edwards
(74) *Attorney, Agent, or Firm* — WPAT, P.C.; Anthony King (57) ABSTRACT

A method for manufacturing a nerve-stimulating and signal-monitoring device includes the steps of forming a first silicon oxide layer on a surface of a flexible substrate; forming a patterned doped p-type poly-silicon layer on the first silicon oxide layer; forming a second silicon oxide layer on the patterned doped p-type poly-silicon layer; forming a circuit layer on the second silicon oxide layer; forming a plurality of openings on the second silicon oxide layer; forming a gold layer on the circuit layer and on the plurality of contact pads on the patterned doped p-type poly-silicon layer; attaching a chip to the plurality of chip pads of the circuit layer by using a flip-chip bonding technology; forming a plurality of through holes on the at least one probe pad; and securely and correspondingly attaching a plurality of stimulation probes into the plurality of through holes.

7 Claims, 15 Drawing Sheets

MANUFACTURING METHOD OF NERVE-STIMULATING AND SIGNAL-MONITORING DEVICE

CROSS REFERENCE TO RELATED APPLICATIONS

This application claims benefit to, and is a Divisional of U.S. patent application Ser. No. 12/767,592, filed on Apr. 26, 2010. The relevant disclosures of the U.S. patent application Ser. No. 12/767,592 are included by reference thereto as if fully set forth herein.

BACKGROUND OF THE INVENTION

1. Field of the Invention

The present invention relates to a nerve-stimulating and signal-monitoring device and system, and relates more particularly to a nerve-stimulating and signal-monitoring device using radio frequency identification technology for communication and built on a flexible substrate, and a system including the same.

2. Description of the Related Art

Traditionally, an array of probes for stimulating nerves and monitoring responsive signals are formed by using a hard silicon substrate. Such an array of probes is heavy and fragile, must be manufactured with high temperature processes, and has a high manufacturing cost. Moreover, the array of traditional probes cannot be suitably designed in accordance with and neatly engage the contour of the body of a subject, and therefore the probes and the body of the subject cannot be properly engaged.

In addition, the array of traditional probes manufactured by using a hard silicon wafer requires an additional device that is used to increase the signal to noise ratios of retrieved signals and establishes impedance matching. Therefore, the building of the array of traditional probes is costly and highly complex.

Further, the array of traditional probes can be integrated with a thin film transistor amplifier to increase the signal to noise ratio and to improve impedance matching characteristics thereof. However, extra processes are required to manufacture the thin film transistor amplifier, increasing the cost and difficulty of manufacturing.

The technology of traditional arrayed probes cannot provide an array of probes that can be simply and cheaply manufactured, that can be suitably designed in accordance with and neatly engage the contour of the body of a subject, and that can increase the signal to noise ratio and improve impedance matching characteristics thereof. Therefore, a new array of probes is required to be developed.

SUMMARY OF THE INVENTION

The present invention provides a method for manufacturing a nerve-stimulating and signal-monitoring device, which comprises the steps of: forming a first silicon oxide layer on a surface of a flexible substrate; forming a patterned doped p-type poly-silicon layer on the first silicon oxide layer, wherein the patterned doped p-type poly-silicon layer comprises a plurality of contact pads; forming a second silicon oxide layer on the patterned doped p-type poly-silicon layer; forming a circuit layer on the second silicon oxide layer, wherein the circuit layer comprises an antenna, a plurality of chip pads, and at least one probe pad coupled to the plurality of chip pads; forming a plurality of openings on the second silicon oxide layer for exposing the plurality of contact pads on the patterned doped p-type poly-silicon layer; forming a gold layer on the circuit layer and on the plurality of contact pads on the patterned doped p-type poly-silicon layer so as to connect the circuit layer to the plurality of contact pads; attaching a chip to the plurality of chip pads of the circuit layer by using a flip-chip bonding technology, wherein the antenna is electrically coupled to the chip; forming a plurality of through holes on the at least one probe pad; and securely and correspondingly attaching a plurality of stimulation probes into the plurality of through holes.

To better understand the above-described objectives, characteristics and advantages of the present invention, embodiments, with reference to the drawings, are provided for detailed explanations.

BRIEF DESCRIPTION OF THE DRAWINGS

The invention will be described according to the appended drawings in which.

DETAILED DESCRIPTION OF THE INVENTION

Figure 1:
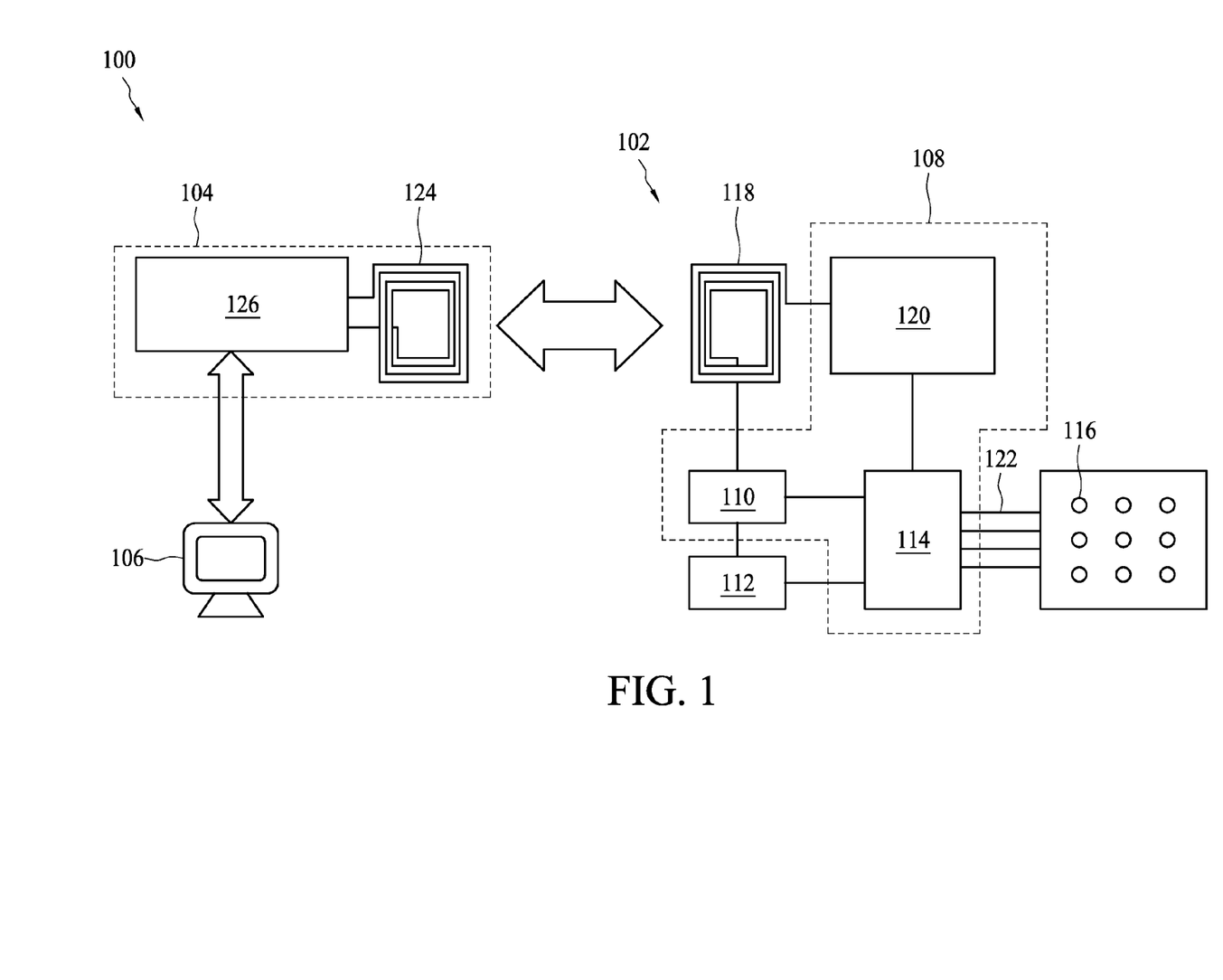
FIG. 1 is a schematic view showing a nerve-stimulating and signal-monitoring system according to one embodiment of the present invention.

FIG. 1 is a schematic view showing a nerve-stimulating and signal-monitoring system 100 according to one embodiment of the present invention. The nerve-stimulating and signal-monitoring system 100 comprises a nerve-stimulating and signal-monitoring device 102, a receiving/transmitting device 104, and a monitor station 106. The nerve-stimulating and signal-monitoring device 102 comprises an antenna 118, a modulation/demodulation module 120, a rectifier module 110, a resistor-capacitor circuit 112, a system on chip (SOC) unit 114, and a plurality of stimulation probes 116, wherein the nerve-stimulating and signal-monitoring device 102 is formed on a flexible substrate. In one embodiment, the modulation/demodulation module 120, the rectifier module 110, and the SOC unit 114 can be integrated in a chip 108. The antenna 118 can be formed on the flexible substrate. The modulation/demodulation module 120 can be disposed on the flexible substrate, configured to demodulate a coded nerve-stimulating received radio-frequency signal from the receiving/transmitting device 104 and to modulate a coded epidermal nerve response signal relating to an epidermal nerve response signal from an epidermal nerve, which is transmitted to the receiving/transmitting device 104. The modulation process is performed by modulating the coded epidermal nerve response signal on a radio carrier wave so as to transmit the coded epidermal nerve response signal via radio communication links.

The rectifier module 110, electrically connected to the antenna 118, is configured to produce direct current voltage by using a radio-frequency signal received by the antenna 118. When the nerve-stimulating and signal-monitoring device 102 is in a passive mode, the nerve-stimulating and signal-monitoring device 102 is driven by the direct current voltage. Generally, to limit the power consumption of the nerve-stimulating and signal-monitoring device 102, the operation mode of the nerve-stimulating and signal-monitoring device 102 is switched to a passive mode from an active mode when the nerve-stimulating and signal-monitoring device 102 is idle, and the nerve-stimulating and signal-monitoring device 102 is activated and operated when receiving a coded nerve-stimulating radio-frequency signal from the receiving/transmitting device 104. Only when a coded nerve-stimulating radio-frequency signal is weak and a coded epidermal nerve response signal is to be sent to the receiving/transmitting device 104, is the nerve-stimulating and signal-monitoring device 102 switched to active mode. Otherwise, a coded epidermal nerve response signal is sent to the receiving/transmitting device 104 in the passive mode.

The SOC unit 114 is separately coupled to the modulation/demodulation module 120, the rectifier module 110, the resistor-capacitor circuit 112, and the plurality of stimulation probes 116. The SOC unit 114 can be driven by the current or the voltage from the rectifier module 110 so that it can operate in the passive mode. The resistor-capacitor circuit 112 can also be formed on the flexible substrate and be configured to provide the SOC unit 114 with a clock signal for driving the SOC unit 114. The SOC unit 114 receives and decodes a coded nerve-stimulating signal from the modulation/demodulation module 120, and obtains and sends a nerve-stimulating electrical probe-driving signal out. The SOC unit 114 transmits the nerve-stimulating electrical probe-driving signal to the stimulation probes 116 via conductive traces 122 such that the epidermal nerves can be stimulated or treated. In the present embodiment, the SOC unit 114 is electrically connected to the modulation/demodulation module 120 so that it can directly decode the coded radio-frequency signal received by the antenna 118. In addition, the above nerve-stimulating and monitoring actions can be applied to a plurality of epidermal nerves one by one in a sequential manner.

In addition, the SOC unit 114 can acquire nerve response signals from epidermal nerves through the stimulation probes 116, thereby monitoring the response of the stimulated or treated epidermal nerves. The nerve response signals acquired by the SOC unit 114 are amplified, analyzed, classified, and encoded, and are then transmitted to the modulation/demodulation module 120. The modulation/demodulation module 120 modulates the coded epidermal nerve response signal with a radio carrier wave to become radio transmission waves. The radio transmission waves are then transmitted, and are received by the receiving/transmitting device 104.

In the present embodiment, the SOC unit 114 can acquire nerve response signals from epidermal nerves through the stimulation probes 116, and then amplify, analyze, classify, and encode the nerve response signals, which are thereafter modulated by the modulation/demodulation module 120, and are transmitted through the antenna 118 to the main station 106 for analysis and monitoring the response of the epidermal nerves.

The receiving/transmitting device 104, configured to transmit/receive a coded nerve-stimulating radio-frequency signal/coded epidermal nerve response signal, comprises an antenna 124 and a receiving/transmitting module 126 electrically connected to the monitor station 106 and configured to modulate coded nerve-stimulating radio-frequency signals and to demodulate epidermal nerve response signals. When the monitor station 106 provides nerve-stimulating electrical probe-driving signals to the stimulation probes 116, the coded nerve-stimulating signals are modulated by the receiving/transmitting module 126 so that they can be transmitted through the antenna 124 to the nerve-stimulating and signal-monitoring device 102. The receiving/transmitting module 126 demodulates the coded epidermal nerve response signals, which are then transmitted to the monitor station 106 for decoding, analyzing, monitoring, and determining the response and the effectiveness of treatment induced by the nerve-stimulating electrical probe-driving signals. In one embodiment, the monitor station 106 comprises codes provided for the nerve-stimulating signals.

Figure 2:
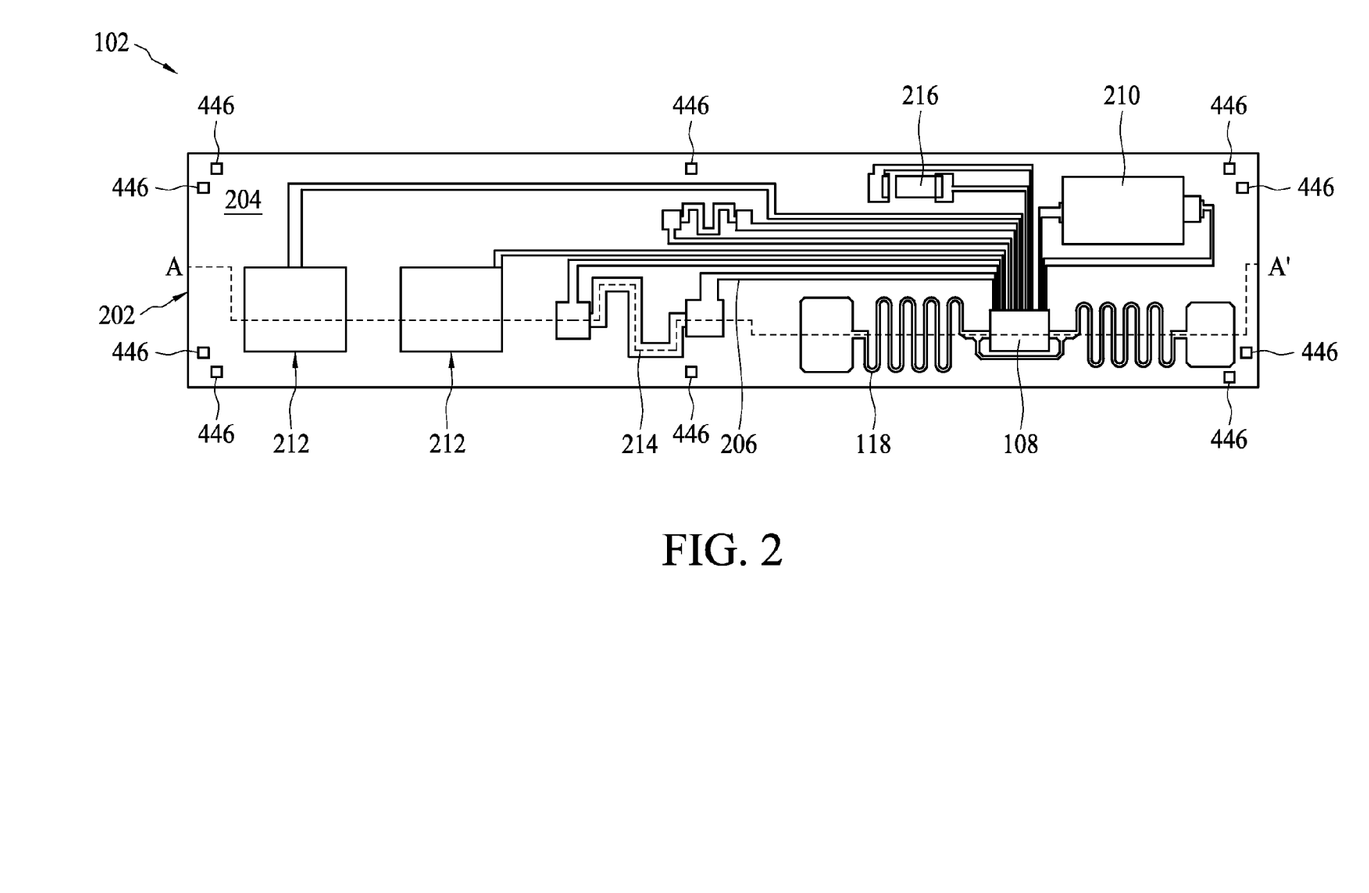
FIG. 2 is a schematic view showing a nerve-stimulating and signal-monitoring device according to one embodiment of the present invention.
Figure 3:
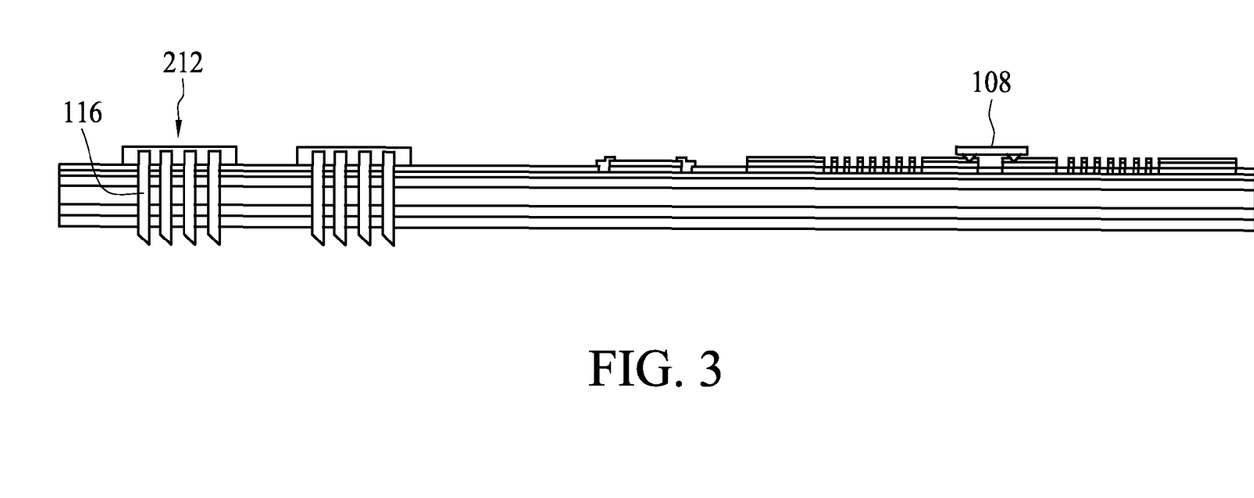
FIG. 3 is a cross-sectional view along line A-A' of FIG. 2.

FIG. 2 is a schematic view showing a nerve-stimulating and signal-monitoring device 102 according to one embodiment of the present invention. Referring to FIGS. 2 and 3, the nerve-stimulating and signal-monitoring device 102, formed on a flexible substrate 202, comprises a flexible substrate 202, a circuit layer 206 formed on a surface 204 of the flexible substrate 202, a chip 108 that is flip-chip bonded to the circuit layer 206, a plurality of groups 212 of stimulation probes electrically connected to the circuit layer 206, and a battery 210 configured as an electrical source when the nerve-stimulating and signal-monitoring device 102 operates in an active mode. On the flexible substrate 202, a plurality of resistors 214 and capacitors 216 formed of doped p-type poly-silicon can be formed. The electrodes of the resistors 214 and capacitors 216, the circuit layer 206, and the dielectric layer between the electrodes and the circuit layer 206 are constituted as thin film passive devices involved in the operation of the nerve-stimulating and signal-monitoring device 102. The circuit layer 206 may comprise an antenna 118 disposed on two opposite sides of the chip 108 and coupled thereto.

In the present embodiment, the chip 108 can be a radio frequency identification (RFID) chip, which can be constructed by integrating the rectifier module 110, the SOC unit 114, and the modulation/demodulation module 120 by using a system in package (SIP) technology. The antenna 118 and the plurality of stimulation probes 116 are formed on the flexible substrate 202 with a chip 108 connected thereto so as to stimulate and monitor biological nerves using a radio transmission link. Referring to FIG. 2, the nerve-stimulating and signal-monitoring device 102 of the present invention may further include a plurality of holes 446 disposed adjacent to four corners of the flexible substrate 202 and allowing a rope to pass through them for retention. Such an arrangement allows the nerve-stimulating and signal-monitoring device 102 to be portable and conveniently used.

Figure 4:
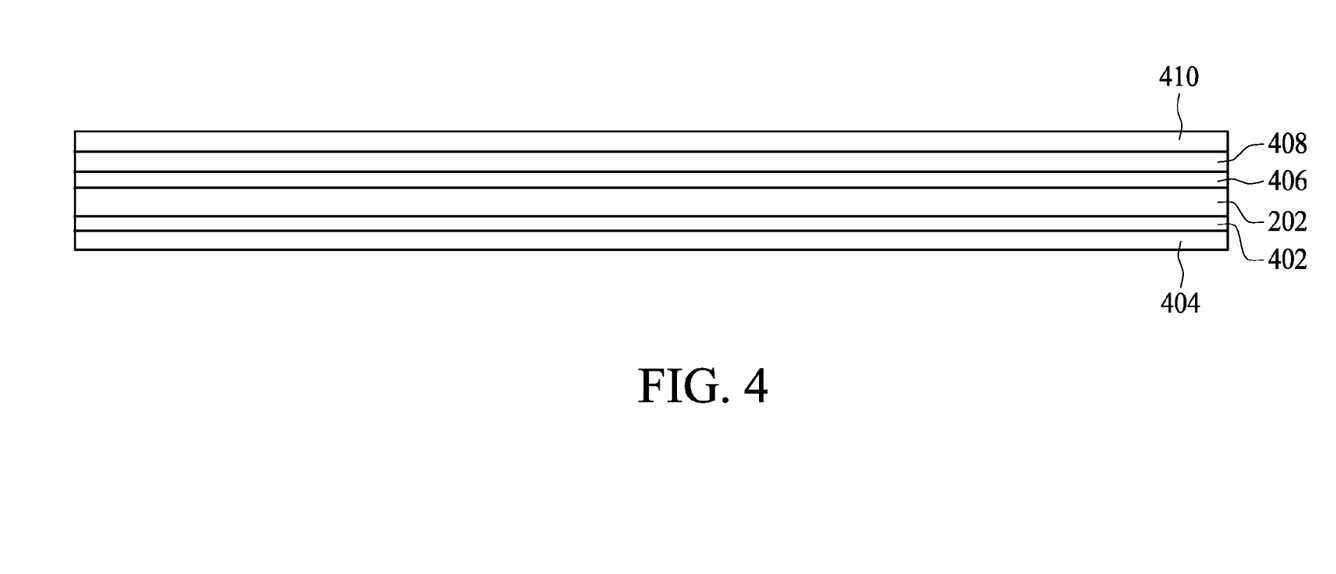
FIG. 4 is a cross-sectional view showing multiple thin films formed on a flexible substrate according to one embodiment of the present invention.

FIGS. 4 to 9B are schematic views showing a method for manufacturing a nerve-stimulating and signal-monitoring device according to one embodiment of the present invention. As shown in FIG. 4, a layer of silicon oxide 402 with thickness of 10 to 20 micrometers is evaporated on the back of a flexible substrate 202 as an isolation and wafer-proof layer for an array of stimulation probes, an antenna, and resistors and capacitors. Next, a positive photoresist layer 404 with thickness of 0.5-5 micrometers is formed and baked for drying. The photoresist layer 404 can protect the silicon oxide 402 and serve as a waterproof layer. On the front side of the flexible substrate 202, a silicon oxide layer 406 with thickness of 1-10 micrometers is deposited by using an evaporation process. Thereafter, a mixed powder of p-type impurity and silicon is deposited on the silicon oxide layer 406 by using an e-gun evaporation process to form a doped p-type amorphous silicon layer with thickness in a range of from 10 to 250 micrometers. Next, a laser is used to anneal the p-type amorphous silicon layer to obtain a doped p-type poly-silicon layer 408, which can be used as a base structure of the electrodes of resistors and capacitors. Finally, a negative photoresist layer 410 with thickness of 0.5-5 micrometers is formed on the p-type poly-silicon layer 408 and baked for drying.

Figure 5:
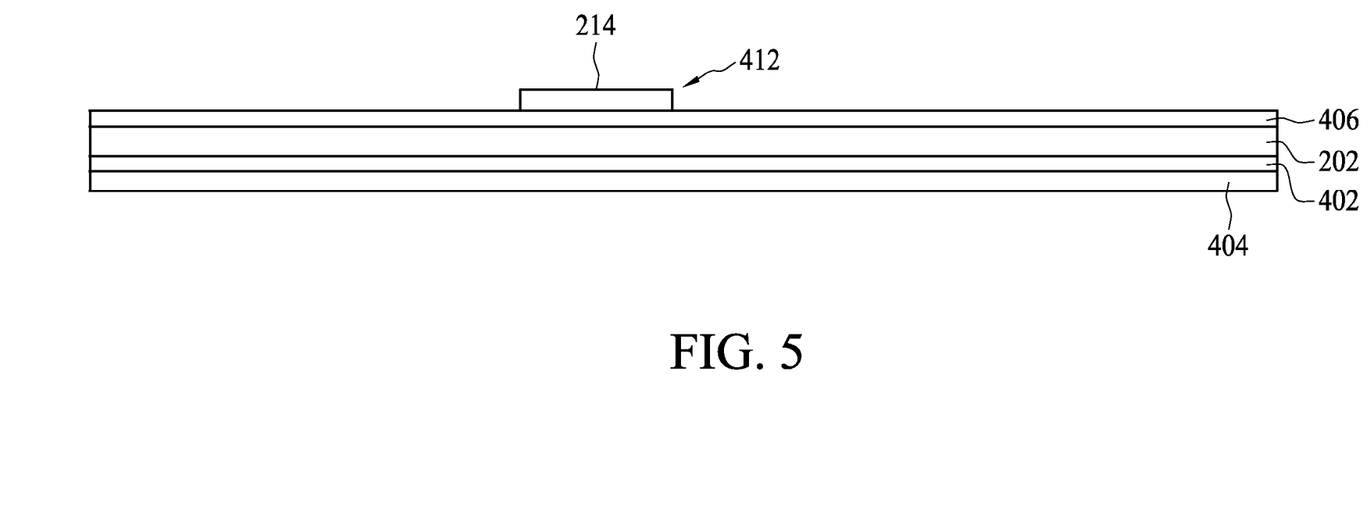
FIG. 5 is a cross-sectional view showing a patterned doped p-type poly-silicon layer according to one embodiment of the present invention.

Referring to FIGS. 4 and 5, a first photomask and a lithographic process are used to define a negative photoresist layer 410 formed on the front side of the flexible substrate 202 for protection of the doped p-type poly-silicon resistor and capacitor structure. The photoresist layer 410 is exposed to ultraviolet light to form long chain polymer components therein. After developing, the unexposed portions of the photoresist layer 410 are removed. Next, the portions of the doped p-type poly-silicon layer 408 not protected by the photoresist layer 410 are etched away by using KOH solution. Thereafter, the protective photoresist layer 410 is removed by acetone or using an ozone ashing process so that a resistor 214 can be formed.

Figure 6:
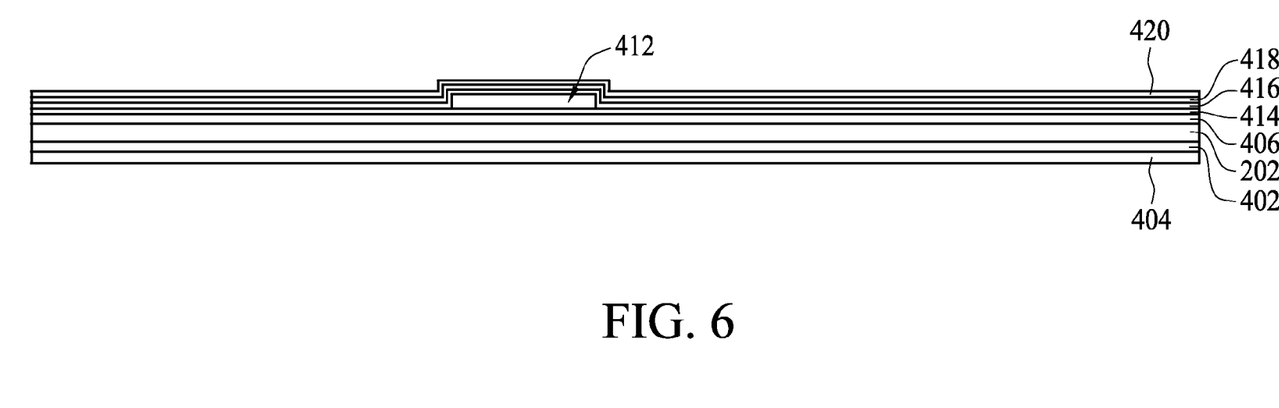
FIG. 6 is a cross-sectional view showing a doped p-type poly-silicon layer and a gold layer formed on the doped p-type poly-silicon layer according to one embodiment of the present invention.

Referring to FIG. 6, a silicon oxide layer 414 with thickness of 1-10 micrometers is deposited on the patterned doped p-type poly-silicon layer 412 as an insulating layer. Next, two metal layers, a chrome layer 416 and a nickel layer 418, are sequentially formed for fabricating an antenna, metal resistors, stimulation probes, and conductive traces for connecting a voltage source and transmitting signals. Thereafter, a layer of negative photoresist 420 with thickness of 0.5-5 micrometers is coated on the two metal layers and is baked for drying.

Figure 7A:
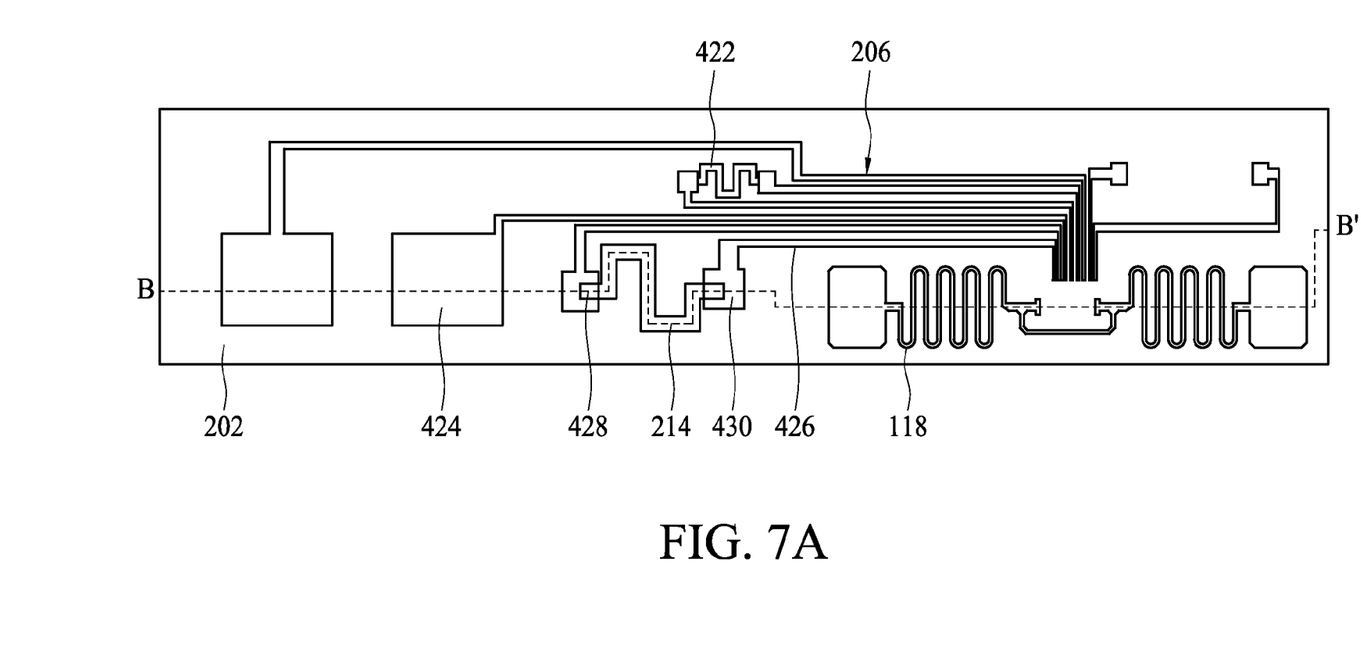
FIG. 7A is a front view showing a circuitry layout on a flexible substrate after a chrome layer and a nickel layer are formed according to one embodiment of the present invention.
Figure 7B:
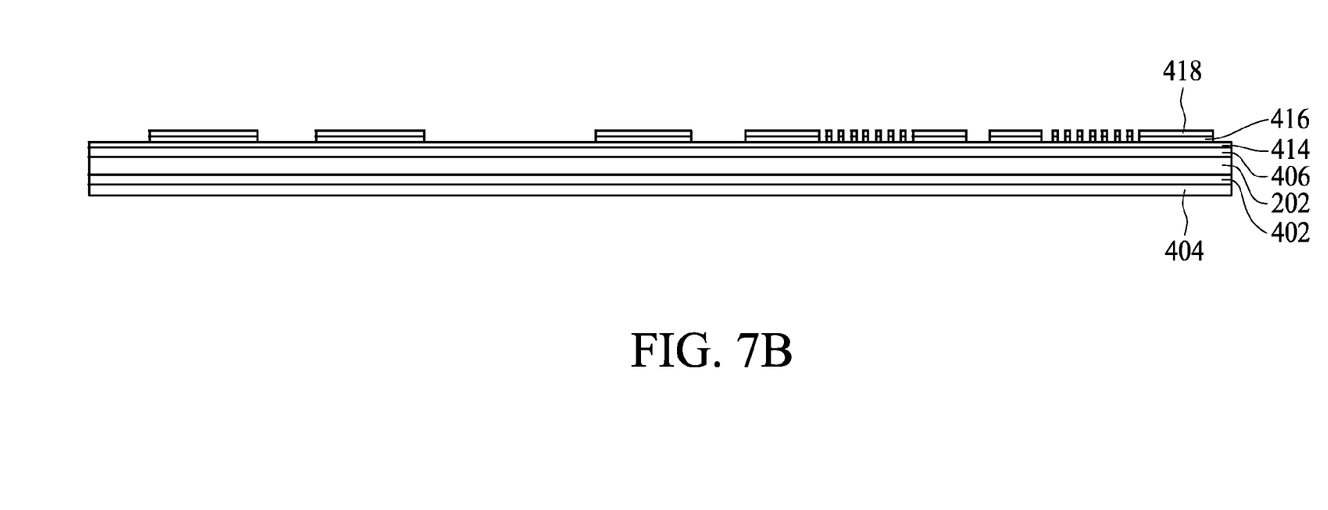
FIG. 7B is a cross-sectional view along line B-B' of FIG. 7A.

Referring to FIGS. 6, 7A, and 7B, a second photomask and a lithographic process are used to define areas including long chain polymer components, which are formed after the negative photoresist 420 is exposed to ultraviolet light. The areas are configured to protect the portions used to form the resistor 422, the antenna 118, the probe pads 424, and electrical traces 426 for connecting a voltage source and transmitting signals. After a developing process, the undefined portions of the photoresist layer 420 are removed. Next, a solution for etching chrome and nickel is used to remove the portion of the chrome layer 416 and the nickel layer 418, which is not protected by the photoresist layer 420. The remaining metal forms the circuit layer 206, which includes the resistor 422, the antenna 118, the probe pads 424, and the electrical traces 426 for connecting a voltage source and transmitting signals. Finally, the photoresist layer 420 is removed by acetone or an ozone ashing process.

In another embodiment, the circuit layer 206 can be manufactured using a method in which a thick photoresist such as SU-8 is defined, and the portions of the photoresist such as SU-8 where the resistor 422, the antenna 118, the probe pads 424, and the electrical traces 426 are located are removed. Next, chrome and nickel are deposited. Finally, the photoresist such as SU-8 is removed by using a lift-off process, and the structures of the circuit layer 206 are left.

Figure 8A:
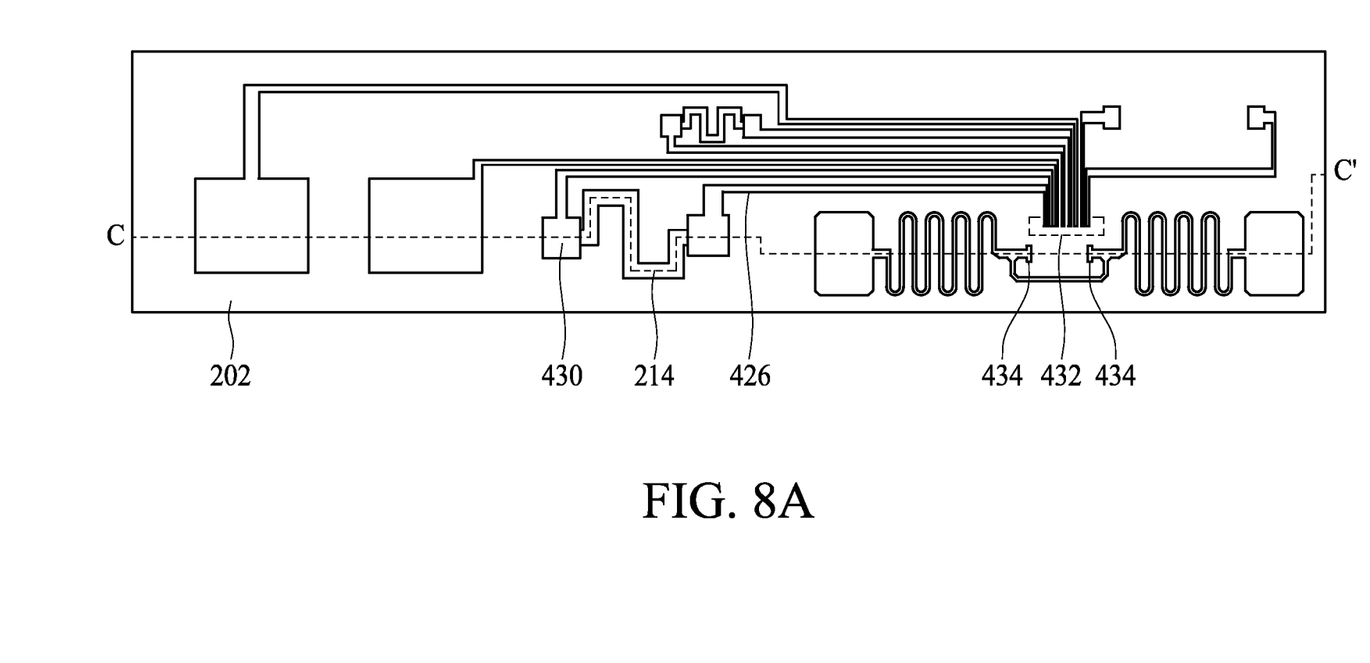
FIG. 8A is a front view showing a circuitry layout on a flexible substrate after a gold layer is formed according to one embodiment of the present invention.
Figure 8B:
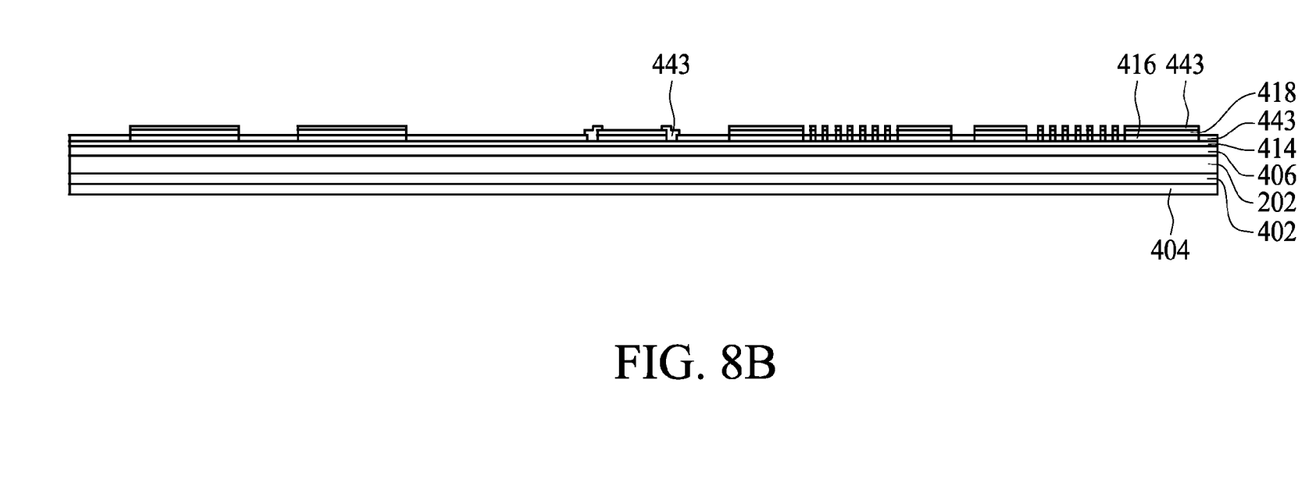
FIG. 8B is a cross-sectional view along line C-C' of FIG. 8A.

As shown in FIGS. 7A, 8A, and 8B, a negative photoresist layer with thickness of 0.5-5 micrometers is coated and then baked for drying. Using the third photomask and a lithographic process, the portions of the contact pads 428 of the resistor 214 for external connection, the antenna 118, the probe pads 424, and the electrical traces 426 for connecting to a voltage source and transmitting signals are defined on the negative photoresist as shown in FIG. 7A. After performing a developing process and etching away the chrome, nickel, and silicon oxide covering the contact pads 428 of the poly-silicon resistor 214, a gold layer 443 with thickness of 0.02 to 0.5 micrometers is formed on the chrome and nickel films on the contact pads 428, the solder pads 430 connected to the contact pads 428 via the electrical traces 426, the antenna 118, the probe pads 424, and the electrical traces 426 for connecting to a voltage source and transmitting signals. The three metal layer structure including chrome, nickel, and gold layers has better electrical conductivity, compared to the traditional film made of silver paste by using screen printing or inject printing technique.

Figure 9A:
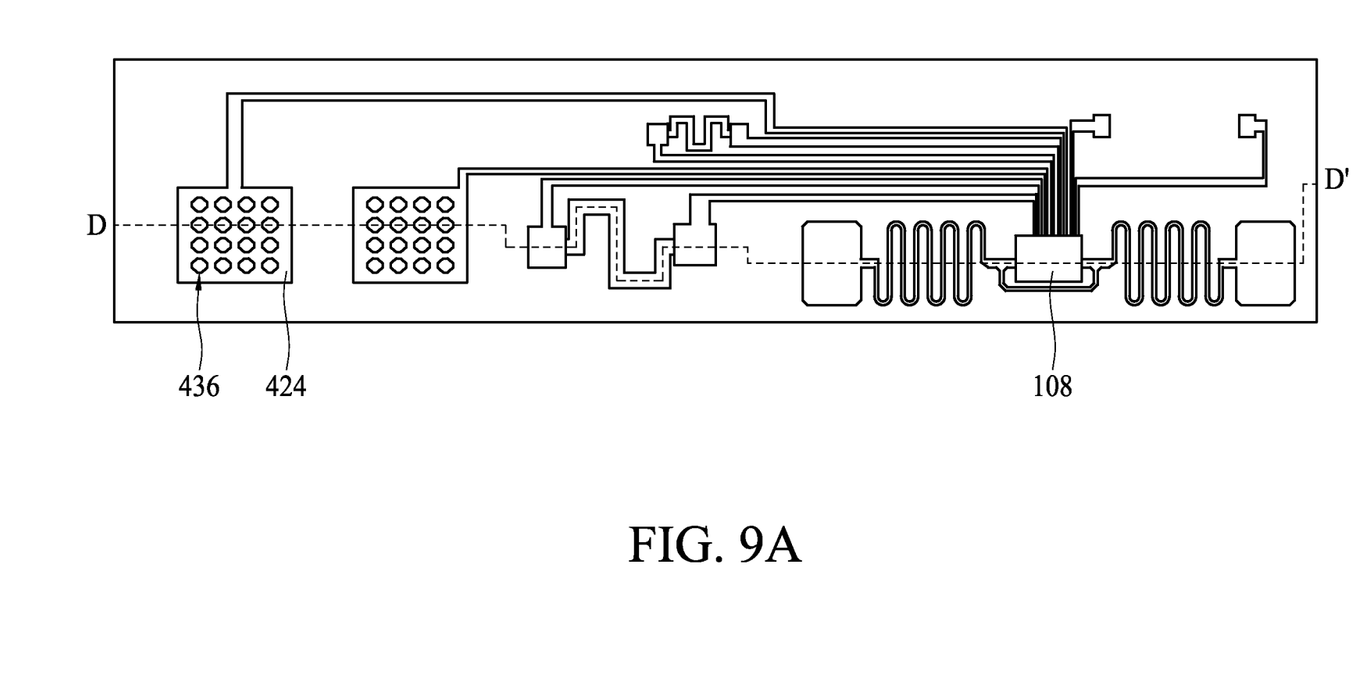
FIG. 9A is a front view showing a circuitry layout on a flexible substrate after a plurality of through holes are formed and a chip is flip-chip bonded according to one embodiment of the present invention.
Figure 9B:
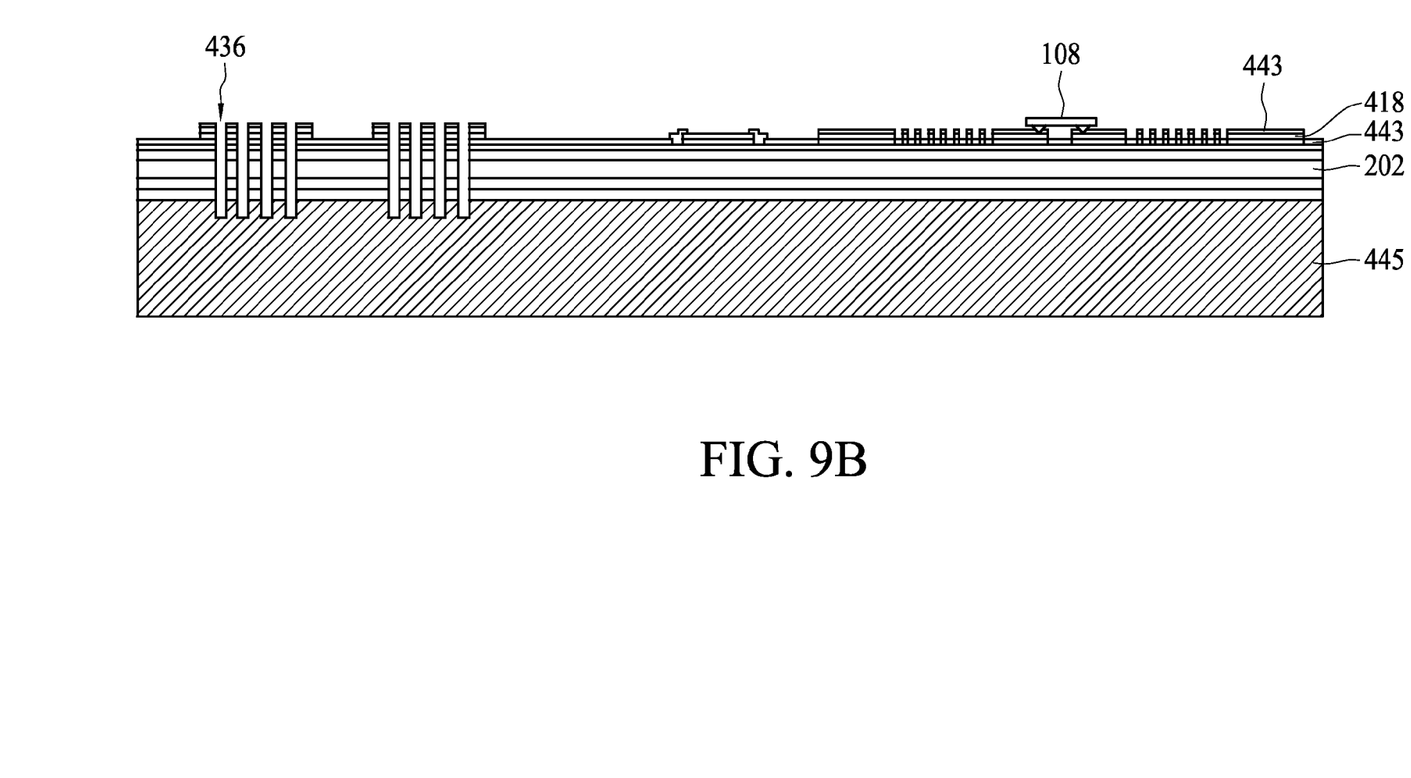
FIG. 9B is a cross-sectional view along line D-D' of FIG. 9A.
Figure 9C:
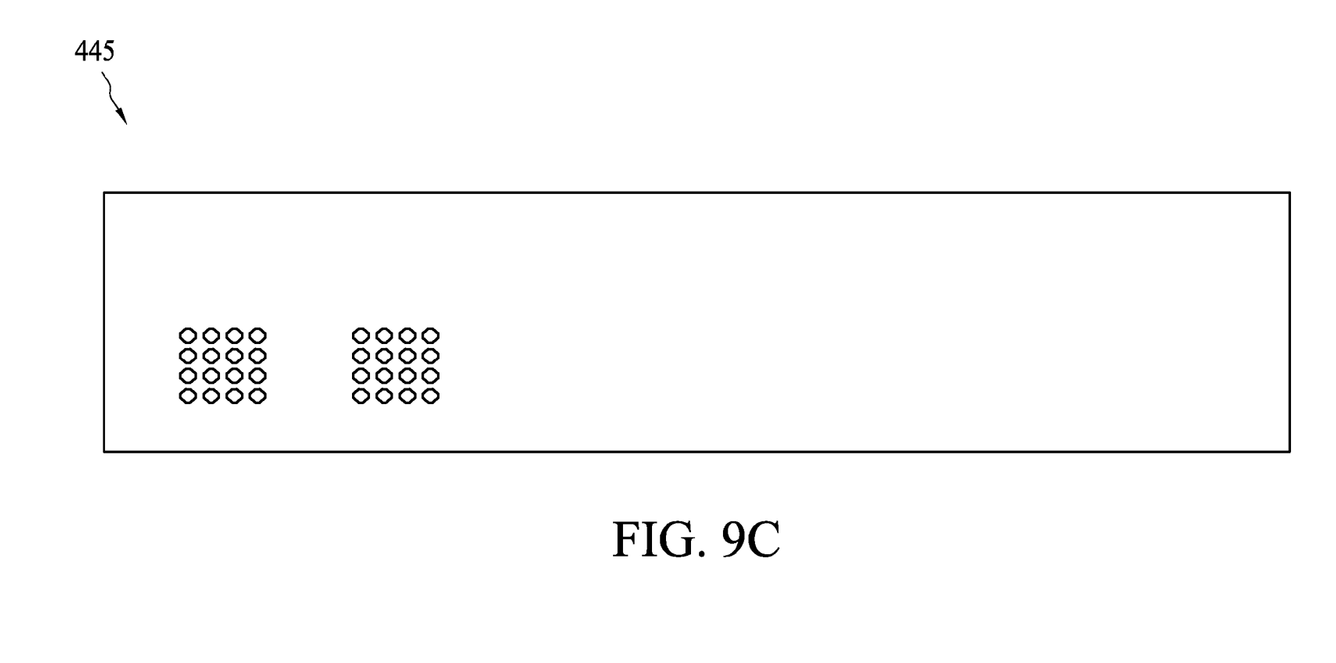
FIG. 9C is a view showing a probe insertion tool according to one embodiment of the present invention.

Referring to FIGS. 8A, 9A, and 9B, metal bumps are respectively formed on chip pads 432 and antenna feeding ends 434 as shown in FIG. 8A. Next, a chip 108 is flip-chip bonded to the chip pads 432 for connecting to a voltage source and transmitting signals and the antenna feeding ends 434 by using a thermal compression welding technique such that the chip 108 is welded on the flexible substrate 202. Thereafter, using a drill, a plurality of suitably sized through holes 436 are formed on each probe pad 424 and can be arranged in a desired manner as shown in FIGS. 9A and 9B. Finally, the plurality of stimulation probes 116 are respectively inserted into the through holes 436. Before the insertion of the stimulation probes 116 into the through holes 436, a probe insertion tool 445 is placed below and aligned with the flexible substrate 202. On the probe insertion tool 445, a plurality of cavities, as shown in FIG. 9C, are formed at locations corresponding to the probe pads 424. After the stimulation probes 116 are inserted through the guiding holes 436 on the flexible substrate 202, the tips of the stimulation probes 116 may engage the bottoms of the cavities. Next, a plier or a punching machine is used to neatly trim the exposed portions of the inserted stimulation probes 116, wherein a predetermined length of each stimulation probe 116 is left to protrude beyond the corresponding probe pad 424 for the requirement of the next screen printing or inject printing process. Finally, a conductive paste, for example a silver paste, is applied on each probe pad 424 and the respective stimulation probes 116 by using a screen printing or inject printing technique for electrical connection.

Figure 10:
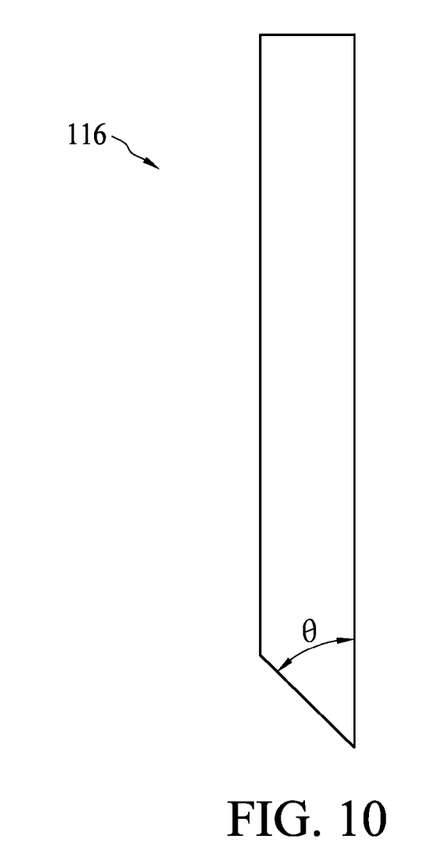
FIG. 10 shows a stimulation probe according to one embodiment of the present invention.

Referring to FIG. 10, before insertion of the stimulation probes 116, the tip of each stimulation probe 116 can be shaped to have a tip angle $\theta$ in a range of from 35 to 55 degrees for piercing the epidermis and dermis during treatment using a plier or a punching machine. Preferably, the tip angle $\theta$ can be 45 degrees. The material of the stimulation probe 116 can be stainless steel, tungsten or nickel chrome wire, and the stimulation probe 116 can be coated with titanium nitride or titanium.

Figure 11:
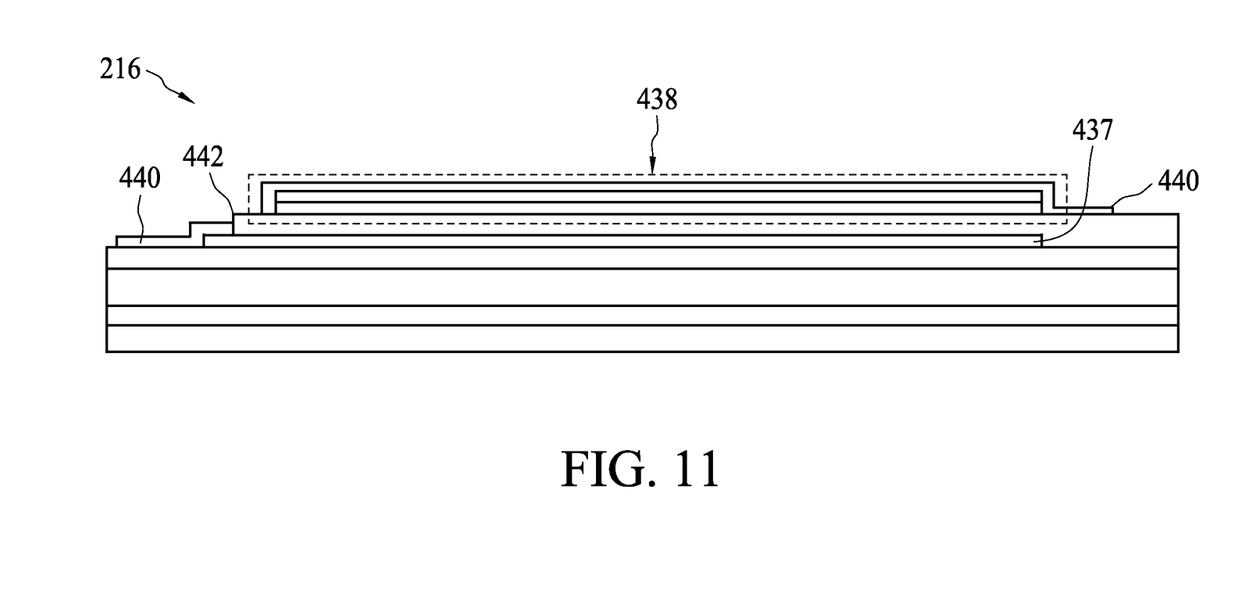
FIG. 11 shows a capacitor having a doped p-type poly-silicon electrode according to one embodiment of the present invention.

Referring to FIG. 11, the capacitor 216 as shown in FIG. 2 can be fabricated by using the above-mentioned processes. Doped p-type poly-silicon can be used to make the lower electrode 437. The chrome, nickel, and gold layers can be used as the upper electrode 438. The gold conductive traces 440 can be used for externally connecting the lower electrode 437 and for externally connecting the upper electrode 438, wherein silicon oxide layer 442 or other dielectric material layer is formed between the lower and upper electrodes 437 and 438. The capacitor 216 can be coupled to the antenna 118 to adjust the resonant frequency of the antenna 118. The capacitor 216 can also be applied in the resistor-capacitor circuit 112 as shown in FIG. 1, or used for power supplies or for filtering signals.

In summary, the present invention proposes a nerve-stimulating and signal-monitoring device and a system using the same. The system uses the RFID technology for communication, and the device includes a flexible substrate, an antenna formed on the substrate by using a printed circuit board manufacturing process, and an array of stimulation probes attached to the flexible substrate. The flexible substrate is integrally disposed with an RFID chip so that the device can provide stimulation signals and monitor the response of stimulation through radio transmission. The technology of the present invention can support remote control of the RFID chip, and sending of different stimulation signals. The response signals acquired by the stimulation probes can be amplified by the amplifier (for example, an instrumentation amplifier) in the SOC unit so as to increase the signal to noise ratio and to eliminate the impedance matching problem. The instrumentation amplifier needs a plurality of externally connected resistors, which can be manufactured on the flexible substrate by using the processes used to manufacture the aforementioned resistor 214 or 422. The externally disposed resistors can reduce the area occupied by the SOC unit, and also resolve the heat dissipation issue that a SOC unit having internally disposed resistors might have. In addition, the flexible substrate allows the stimulation probes to be neatly placed in accordance with the outline contour of a subject's body such that the effective contact can be improved.

The above-described embodiments of the present invention are intended to be illustrative only. Numerous alternative embodiments may be devised by persons skilled in the art without departing from the scope of the following claims.

What is claimed is:

1. A method for manufacturing a nerve-stimulating and signal-monitoring device, comprising steps of:
   forming a first silicon oxide layer on a surface of a flexible substrate;
   forming a patterned doped p-type poly-silicon layer on the first silicon oxide layer, wherein the patterned doped p-type poly-silicon layer comprises a plurality of contact pads;
   forming a second silicon oxide layer on the patterned doped p-type poly-silicon layer;
   forming a circuit layer on the second silicon oxide layer, wherein the circuit layer comprises an antenna, a plurality of chip pads, and at least one probe pad coupled to the plurality of chip pads;
   forming a plurality of openings on the second silicon oxide layer for exposing the plurality of contact pads on the patterned doped p-type poly-silicon layer;
   forming a gold layer on the circuit layer and on the plurality of contact pads on the patterned doped p-type poly-silicon layer so as to connect the circuit layer to the plurality of contact pads;
   attaching a chip to the plurality of chip pads of the circuit layer by using a flip-chip bonding technology, wherein the antenna is electrically coupled to the chip;
   forming a plurality of through holes on the at least one probe pad; and
   securely and correspondingly attaching a plurality of stimulation probes into the plurality of through holes.

2. The method of claim 1, wherein the step of forming a circuit layer on the second silicon oxide layer comprises steps of:
   sequentially forming a chrome layer and a nickel layer on the second silicon oxide layer; and
   patterning the chrome layer and the nickel layer to form the circuit layer.

3. The method of claim 1, wherein the step of forming a circuit layer on the second silicon oxide layer comprises steps of:
   forming a patterned photoresist layer on the second silicon oxide layer;
   sequentially forming a chrome layer and a nickel layer on the patterned photoresist layer; and
   lifting off the patterned photoresist layer.

4. The method of claim 1, wherein the first and second silicon oxide layers have a thickness in a range of from 1 to 10 micrometers.

5. The method of claim 1, wherein the patterned doped p-type poly-silicon layer is of a thickness in a range of from 10 to 250 micrometers.

6. The method of claim 1, wherein the gold layer is of a thickness in a range of from 0.01 to 0.5 micrometers.

7. The method of claim 1, wherein the flexible substrate further comprises a plurality of holes disposed adjacent to four corners thereof allowing a rope passing therethrough for retention.

* * * * *